(12) United States Patent
Berliner et al.

(10) Patent No.: US 6,555,531 B1
(45) Date of Patent: Apr. 29, 2003

(54) WEIGHT PROMOTING COMPOSITION, METHOD, AND PRODUCT

(75) Inventors: David L. Berliner, Atherton, CA (US); Louis Monti, Salt Lake City, UT (US); Clive L. Jennings-White, Salt Lake City, UT (US)

(73) Assignee: Pherin Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 09/475,328

(22) Filed: Dec. 30, 1999

(51) Int. Cl.[7] .............................. A61K 31/57; A61P 3/00
(52) U.S. Cl. ..................... 514/182; 424/434; 424/45
(58) Field of Search ............................ 514/170, 167, 514/182, 178, 179, 181

(56) References Cited

U.S. PATENT DOCUMENTS

| | | | |
|---|---|---|---|
| 3,917,831 A | * | 11/1975 | Grunwell et al. ............ 424/243 |
| 3,946,052 A | * | 3/1976 | Crowe et al. ............ 260/397.5 |
| 5,792,757 A | * | 8/1998 | Jennings-White et al. .. 514/170 |

FOREIGN PATENT DOCUMENTS

| WO | WO 97/39596 | 10/1997 |
|---|---|---|
| WO | WO 98/03207 | 1/1998 |

OTHER PUBLICATIONS

Williams & Wilkins, Stedman's medical dictionary, 25th Edition, 1990, p. 1728.*
Williams and Wilkins, Stedman's Medical Dictionary, 26th Edition, 1995, p. 1258.
W.B. Saunders Company, Dorland's Illustrated Medical Dictionary, 28th Edition, pages 1189 and 1191.
L. Monti Bloch, et al., "The Human Vomeronasal System", *Annals of the New York Academy of Sciences*, New York, NY, vol. 855, 1998. pp. 373–389.
L. Monti–Bloch, et al., "Effect of Putative Pheromones on the Electrical Activity of the Human Vomeronasal Organ and Olfractory Epithelium", *Journal of Steroid Biochemistry and Molecular Biology*, GB, vol. 39, No. 4B, Oct. 1991 (1991–10), pp. 573–582.

* cited by examiner

*Primary Examiner*—Edward B. Webman
(74) *Attorney, Agent, or Firm*—Heller Ehrman White & McAuliffe LLP

(57) ABSTRACT

Pregnanes of formula I, and pharmaceutical compositions and products containing them, are useful in weight promotion by administration to the vomeronasal organ.

22 Claims, No Drawings

WEIGHT PROMOTING COMPOSITION, METHOD, AND PRODUCT

BACKGROUND OF THE INVENTION

This invention relates generally to weight promotion. Weight promotion is desirable in treating many medical and physiological conditions as well as for sports training and other activities. When weight promotion is not possible or effective in weight critical conditions, other means of treatment are used to limit the clinical effects of compromised weight.

Weight Promoting Approaches

Weight promotion can include increasing weight, maintaining weight, or slowing weight loss. There are many medical conditions which call for weight promotion. By example, in such conditions as anorexia nervosa, weight loss can lead to severe illness. Similarly, the frail elderly often suffer loss of appetite due to multiple factors such as anosmia, lack of exercise and depression. Wasting in the elderly constitutes a serious challenge in gerontology.

The depressive component of anorexia nervosa and elderly wasting can be treated, in some cases successfully, with counseling and antidepressant drugs. However, lack of appetite with resulting body emaciation often persists. Modification of body form perception in anorexia nervosa, and engaging activities for the elderly often assists in reversing these conditions. Forced feeding is resorted to in serious cases. While these and other clinical approaches are successful in some cases, disability and even death may occur in others.

Other clinical conditions benefit from weight promoting therapy. Wasting in cancer patients, especially those undergoing chemotherapy, is a challenge to oncologists. Morning sickness can be so severe as to require prolonged hospital stays, putting both the mother and unborn child at risk. Depressive conditions can lead to disinterest in food, with the resulting weight loss in turn exacerbating the underlying depression.

Carefully selected diets offered at optimal times of day are helpful in encouraging adequate food consumption in cancer patients and pregnant women suffering from morning sickness. These approaches are also useful with depressed patients, especially when coupled with anti-depressant drugs.

Low weight, especially in the frail elderly, is a contributing factor to osteoporosis and muscle wasting. The health problems attending major bone breakage and spinal cord collapse caused by these conditions are a serious public health challenge. Many therapy approaches, such as high calcium diets and exercise, provided some slowing of the effects of these challenging diseases. However, current intervention efforts are typically only partially effective in limiting the adverse effects of these conditions.

To promote weight gain among athletes, supercaloric dietary supplements are often used to provide weight gain and muscle mass increase. A disadvantage to dietary supplements is that they often satiate the appetite.

Use of systemic steroids has been previously employed to increase muscle mass. Systemically administered steroids, while highly effective in promoting body mass, have numerous side effects, including toxicity and aggressive behavior. Because of these attendant problems, systemic steroid use has been banned from most sporting events. These drugs are now strictly controlled or illegal in most jurisdictions.

Advantages of VNO Administration of Pharmaceuticals

Some of the present inventors have discovered a class of pharmaceuticals which directly stimulate the vomeronasal organ, hereinafter the VNO. Substances which act through the vomeronasal system are defined as vomeropherins. Because this class of pharmaceuticals are administered directly to the VNO, vomeropherins do not need to enter the systemic circulation in order to exert their therapeutic effects. Instead, when administered to the VNO, such as by a nasal spray, vomeropherins stimulate the VNO directly, triggering a response in the brain, such as in the hypothalamic regions.

Nasally administered vomeropherins do not need to cross the biological barriers that are associated with systemic drug absorption and distribution in order to produce the desired therapeutic effect. Consequently, this class of pharmaceuticals enjoys a rapid onset of action. In addition, because typically only minute quantities of vomeropherins are required to induce a biological response, both production costs and the potential for adverse side effects are minimized.

One characteristic of vomeropherins is that they are typically associated with reproductive factors. In certain treatment schemes, this aspect of vomeropherins is very useful. However, this gender specificity can prove a disadvantage for general applications (Monti-Bloch et al, *J. Steroid Biochem. Molec. Biol.* 39, 573–582 (1991)). Additionally, many of the reproductive effects in female patients are limited to pre-menopausal women.

There is a long standing need for a weight promoting pharmaceutical that would, be effective in weight compromised patients of different ages and genders. It would be an important advancement in the art if such a weight promoting pharmaceutical could be developed which had the advantages of VNO administration.

SUMMARY OF THE INVENTION

The present inventive weight promoting composition is an important advancement in the field of weight promotion. The inventors have unexpectedly discovered a VNO administered pharmaceutical composition which promotes weight gain in all ages and both genders, while avoiding problems of systemic administration.

The special qualities of VNO drug administration provide the weight promoting composition of the present invention with unique advantages over currently available pharmaceuticals and feeding regimens. In many cases the inventive composition acts synergistically with these prior art approaches. The activity of the inventive composition is not limited to one gender, or pre-menopausal women, and thus enjoys broad applicability.

It is an object of the present invention to provide a weight promoting composition which is effective when administered through the VNO in a broad range of individuals.

It is a further object of the present invention to provide a weight promoting composition which is effective in promoting weight in clinical conditions such as, for example, anorexia nervosa, anosmia, wasting in elderly, AIDS, cancer, morning sickness, osteoporosis, and childhood eating disorders.

It is yet a further object of the present invention to provide for increase muscle and general body mass in athletes, such as for wrestling, body building, football, hockey, weight lifting training and events.

It is an additional object of the present invention to provide a weight promoting effect by means of administration to the VNO, so as to avoid systemic exposure to the active compound.

DETAILED DESCRIPTION OF THE INVENTION

The present inventive composition, method, and product allow, for the first time, weight promotion without the disadvantages of systemic exposure to a drug. This special advantage is accomplished by administration of the pregnane vomeropherin of formula I, or a pharmaceutical composition containing it, to the VNO.

The present invention was made when the inventors unexpectedly discovered that these compounds, when administered to the VNO, promotes weight gain. The compounds of the present invention are effective in all ages and genders.

The vomeropherins which can be appropriately used in the present invention are pregnanes of the formula:

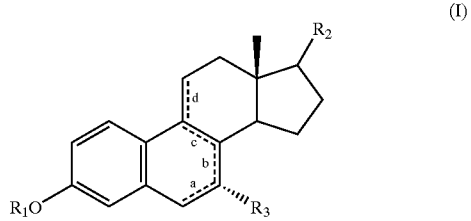

(I)

where:
$R_1$=H, $C_{1-4}$ alkyl, $C_{1-4}$ alkanoyl, $SO_3H$, or salts thereof,
$R_2$=$C_{1-4}$ alkyl,
$R_3$=H or methyl,
and one or two non-adjacent members of a, b, c, and d are optional double bonds.

The special qualities of VNO drug administration provide the weight promoting composition, method, and product of this invention with unique advantages over currently available pharmaceuticals and feeding regimens. Surprisingly, the activity of the inventive composition, method, and product is not limited by age or gender.

Target Conditions and Patient Groups

Diseases Associated with Weight Loss

Anorexia Nervosa. One important embodiment of the weight promoting method of the present invention is the treatment of anorexia nervosa. Among the many pharmacological uses of the present invention, anorexia nervosa is a particularly important application. A disease which has long been recognized as prevalent in pubertal girls, anorexia is now identified as affecting at least 1% of American males. Anorexia nervosa is a challenging disease of complex etiology, characterized by a distorted perception of body weight, horror of eating, and loss of appetite. It typically has a psychiatric aspect, including depression, beyond a disinterest or actual fear of eating. In some cases, anorexic patents display bulimic behavior, i.e. binge eating followed by resort to self-induced vomiting.

Sadly, even when the psychiatric aspects of the disease are alleviated by antidepressant drugs, the disgust with food often continues. In very serious cases, this persistent failure of appetite results in fatalities, which have been reported as occurring in 5% of such patients.

The subnormal weight of the patients can by itself exacerbate an underlying depression, or even be a primary cause of depression. Listlessness and other effects of starvation mirror and support the clinical depression.

In those patients who survive their anorexia, there are often long term sequelae. Especially when the patient suffers from the disease as an adolescent, permanent bone fragility, amenorrhea, and infertility can result. In the case of attendant bulimia, deteriorated tooth enamel and esophageal scaring can occur.

In some cases force-feedings of various types are used in an effort to counter the ill effects of appetite failure. This approach has potential problems with injury, and can worsen patient-care taker relations. Additionally, patients will often resort to self-induced vomiting to circumvent forced feedings.

The elegant approach of the present invention is to induce a desire to eat in the patent using the inventive pharmaceutical composition. This allows appropriate treatment without often self-defeating forced eating. Forced eating can in fact serve to worsen eating disorders.

With early treatment, the method of the present invention may be sufficient in itself to alleviate or even cure anorexia nervosa. When underlying depression or body size misperception are present, systemic or VNO antidepressants and psychological counseling and body image modification can be used as adjunct therapy to the present weight enhancing method.

Disease-Associated Wasting. Many serious illnesses are associated with wasting. General wasting secondary to these conditions often fall under the term cachexia. Wasting associated with serious illness can cause discomfort, depression and lethargy. The wasting which can attend serious illness often acts to exacerbate the patient's many difficulties with the primary disease.

Resort to tube feeding, such as in nursing home environments, has disadvantages. Tube feeding requires increased patient care. The tube feeding procedure and devices can also cause patient discomfort. Also, the lack of roughage available in such feeding approaches may result in poor bowel mobility. For the bedridden, the loss of patient involvement in the pleasurable activity of natural eating may lower morale.

HIV/AIDS. HIV patients who have developed serious symptoms often suffer from cachexia. The general effects of the present invention to promote weight in these patents will be very useful in the management of AIDS. The dosing of AIDS patients with the inventive weight promoting composition can be timed to increase appetite during the times of day most amenable to eating adequate amounts of food. Also, AIDS patients can use the present invention to provide increase weight gain prior to a weight challenging treatment, such as chemotherapy.

Renal Disease. Renal disease and attendant dialysis treatment is often associated with wasting. This wasting can complicate the health management of already compromised individuals. By providing weight maintenance, the present weight promoting invention is an important adjunct therapy for renally compromised individuals.

Wasting secondary to renal disease is particularly harmful when it affects growing children, and in such cases can lead to a permanently smaller stature. Several different therapies have been used in an effort to circumvent long term side effects of pediatric renal disease. Most recently human growth hormone has been employed to stimulate appropriate growth in these children. However, there are concerns about toxicity and other implications of chronic exogenous HGH exposure.

The present invention is an important alternative approach to human growth hormone exposure to provide improved or normal adult stature in children with chronic renal disease. The inventive composition, method, and product can be administered prophylactically to avert potential wasting. When the present invention alone is not able to fully compensate for growth failure, it can be used in adjunct therapy with HGH, allowing a lower exposure level of the more toxic pharmaceutical.

Cancer. As with AIDS patients, cancer patients frequently suffer from cachexia during the severe stages of the disease. This wasting can produce extreme discomfort and complicate treatment efforts. Additionally, disinterest in food curtails a positive, enjoyable activity for bedridden patients. The present inventive composition, method, and product can be used to ameliorate existing cachexia, or can be administered prophylactically to avert this potential wasting.

Further complicating the treatment of cancer patients is the aversion to eating which frequently accompanies chemotherapy treatment. Often, clinically optimal chemotherapy treatment must be limited or curtailed both in frequency, dosage, and duration because of attendant eating dysfunction. By timing the dosages of the present invention to allow a period of weight gain prior to scheduled chemotherapy, a more appropriate schedule of therapy is possible. Additionally, post chemotherapy food aversion can be limited or alleviated.

Metabolic Disorders. Several metabolic disorders are associated with wasting. For instance, diabetes and thyroid over-activity can lead to a drop in patient body weight. The primary treatment of these conditions is providing specific therapy, such as oral medication or insulin injection for severe diabetes cases. However, the present invention can be used as adjunct therapy to these primary treatment methods to enhance weight retention, or correct undue weight loss secondary to these conditions. Additionally, the present composition, method, and product can be administered prophylactically to avert potential wasting.

Eating Disorders. Eating disorders can be associated with a psychological state or a physiologically predisposing condition. Depression, as well as anxiety and stress, can have eating disorders as a side effect. In some cases, these disorders are self-correcting, such as when stressful situations are resolved. However, eating disorders can progress to unhealthy levels when the underlying condition persists. As with anorexia, a particularly dramatic form of eating disorder, the sequelae can be serious.

The frail elderly are often predisposed to physiological challenges which exacerbate poor eating. Factors such as anosmia and lack of physical activity serve to, further undercut weight maintenance in these individuals. For instance, physical frailty complicated by osteoporosis can lead to isolation from family and friends, and limitation of beloved activities. These factors predispose the frail elderly to depression.

The present invention can be used to promote weight in these weight challenged individuals. It can be administered prophylactically at the first sign of weight loss to avert potential wasting. Larger dosages can be provided prior to a particular challenge, such as surgery, to increase body mass. Such an effect will improve the likely outcome of the surgery.

Childhood Eating Disorders. Childhood eating disorders pose a serious challenge to the pediatrician. These feeding disturbances are manifested by persistent failure to eat adequately with significant failure to gain weight or significant loss of weight over at least one month. Onset of these disorders occur before age six. The loss of weight from those disorders is not exclusively due to an associated gastrointestinal or other general medication conditions, such as esophageal reflux.

In infants less than 18 months old, these eating disorders are normally characterized as "failure to thrive". This term has been used for over 60 years to refer to growth retardation in infants. The "failure to thrive" feeding disorder of infancy comprises 1–5% of admissions to pediatric hospitals. One study found that about two thirds of these cases had both organic and psychological factors present.

A variety of combinations of treatments are normally prescribed for such disorders. Psychotherapy for the mother is used to increase her emotional availability to her infant. Behavioral techniques can be used to diminish maladaptive behaviors in the infant's eating habits. When complicated by rumination and hiatus hernia, the infant is kept upright during and after feedings. Surgical repair may be consider if growth retardation is severe. These complex approaches require a treatment team.

The present invention represents an important adjunct to current therapies for childhood eating disorders. By encouraging appetite and weight gain, the inventive pharmaceutical composition provides both motivation to eat and weight gain necessary to sustain appropriate growth in these compromised infants. It may also allow the child to stay with their mother while she is improving her maternal skills, avoiding disruption of the family unit.

Anosmia. Anosmia is an appetite disorder which occurs when patients have a diminished sense of taste and/or smell. Over time there is typically a degeneration of the olfactory organs. As a result, anosmia can be an important factor in frail elderly wasting. Anosmia can also occur secondary to injury or illness, thus effecting other patient groups as well.

Because the normal inducers of appetite are diminished in anosmia, individuals suffering from this disorder often have difficulty maintaining their body weight. The weight promoting effect of the present invention will help such individuals maintain a normal appetite and body weight.

Morning Sickness. The present invention can also be used for direct treatment of weight compromising morning sickness. This condition tends to be at its height in the first trimester of pregnancy, and is often associated with HCG production. However, queasiness and inability to eat can last throughout the pregnancy. Efforts to provide relief from the often serious effects of morning sickness have included thalidomide treatment, predominately in Europe. Unfortunately, the first trimester is a sensitive period in gestation, and many children were born with severe birth defects secondary to this treatment.

Because of the legacy of thalidomide usage, there is a long felt need for an effective method of weight promotion in mothers during the first trimester of their pregnancies, which avoids fetal exposure to the medication. The present weight promoting invention provides this needed therapy.

As described in the "single dose" section below, it is possible to time the administration of the inventive composition, method, and product to optimize the weight promotion effects of the present invention. The aversion to eating associated typically with the first trimester of pregnancy may be partially or fully offset by this administration.

In cases of pregnancy associated food aversion, a customized dosage scheme can improve the results of the present invention. It is a current standard approach that, during the period of day when nausea abates somewhat, pregnant women are encouraged to eat as much as is possible short of triggering vomiting. This approach would be supported by timing the administration of the present invention to encourage eating during the period where food ingestion is more tolerable.

Weight Challenging Situations

Small Builds and Osteoporosis. The prevalence of osteoporosis in both women and men represents a very serious epidemiological challenge. This condition causes diminution in stature, with breakage of major bones, such as the pelvic girdle, through progressive loss of bone mass. Ultimately, this progressive compromise of the skeletal system can impinge on internal organs, exacerbate other serious conditions, and directly or indirectly lead to death. For instance, hip breakage in older women has a high association with subsequent death from heart attack within twelve months of the breakage.

Currently estrogen replacement therapy is used prophylactically in post menopausal women. Estrogen replacement therapy limits the progression of osteoporosis to varying degrees. Additionally, drugs which limit the effects of osteoclastic activity are used to slow, and sometimes restore, loss of bone calcium. High dietary calcium is also used to promote bone density.

Small, thin body types, especially in women, are a major factor in predisposition to osteoporosis. Fear of bone-breakage promotes a sedentary lifestyle. This sedentary lifestyle in turn tends to limit appetite, thus putting body mass at risk. In the frail elderly, anosmia is an added factor in the constellation of conditions predisposing to lower body mass.

The present weight promoting invention is useful in promoting optimal body mass where there is a predisposition to osteoporosis; and can be used as adjunct therapy with estrogen replacement and other therapies. The invention is particularly useful in treatment of cases where exogenous estrogen treatment is counter-indicated, as in women with a history of breast cancer. Also, the present invention will allow the administration of extraneous estrogen at more moderate levels, diminishing attendant risks.

Prophylactic Weight Gain. The present invention can provide an increase in weight prior to weight challenging activities. For instance, severely underweight women can run a severe risk to themselves and their unborn child if challenged by serious morning sickness. Such women will often be admitted to the hospital with this condition, in part due to the potentially serious effects of starvation on both mother and unborn child. Also, underweight women often have irregular reproductive cycles and an increase in weight can improve the chance of a desired pregnancy.

By use of the invention, slightly built women contemplating pregnancy can increase their weight prior to conception, both increasing their chances of early conception and circumventing in some cases the potential sequelae to morning sickness mentioned above. Additionally, because the administration is non-systemic, there are no attendant risks to a fetus if the women becomes pregnant during the period of treatment.

Sports Applications. There are a wide range of situations in which an increase in body mass is desirable. By example, current approaches to building body mass for sports activities are used in wrestling, body building, football, hockey, weight lifting, and other sports calling for an increase of body mass to optimize performance.

This weight promoting invention can be used to replace a number of these prior art approaches, while avoiding many of their attendant problems. Alternatively, the effects of the present invention can be supplemented by concurrent use of prior art methods.

Self-forced eating by athletes has been a method used for thousands of years to increase body mass, such as with Sumo wrestling. More recently, supercaloric supplements have been used to increase the weight gain effects over those from a standard diet.

One disadvantage to these approaches is that, through normal metabolic regulation, eating beyond normal hunger prompters satiates the appetite. This natural feedback inhibition discourages further eating. Self-forced feeding also results in lower metabolism and sedentary behavior, further off-setting weight promoting effects of this approach. Additionally, eating habits which force eating in the face of satiety may be established during an individual's athletically active years. These habits lead to obesity when an athlete later adopts a more sedentary life style.

Athletes have also resorted to the used of systematically administered steroids to promote body-building. These powerful drugs have now been banned at most competitive events. To enforce these bans, mandatory urine testing for steroid use is now standard.

While initially legal, many systemic steroid drugs are now controlled substances. Individuals who used such drugs before their change in status often continue their use. This use risks criminal prosecution with potential jail terms and loss of employment.

Besides the perception that systemic steroid use gives an unfair advantage in sporting events, there is great concern about the numerous side effects of high-dose systemically administered steroids, including toxicity and aggressive behavior. Especially in young athletes, side effects can produce heart problems and other serious developmental complications.

The present weight promoting invention provides the advantage in sports of a large body mass without the attendant disadvantages and side effects of current approaches.

Systemic exposure to synthetic steroids is eliminated. Additionally, weight increases can be accomplished before the start of the sports season, with a more normal weight level being maintained during the balance of the year. Avoiding chronic self forced feeding beyond satiety avoids establishment of unhealthy eating habits.

Administration

Broad Range of Patient Groups. The activity for the invention in men is similar to that in women. When tested by electrovomerogram, men showed an average reaction of 30 mV and women a reactions of 50 mV (see Example 2 below).

Any difference in activity of the invention between genders will not preclude men from enjoying the benefits of the invention's weight promoting qualities. Considering the strength of VNO response to the invention, there may be little or no need for dosage modification in men. Modest gender variations in responses are likely to be unimportant in face of the robust effects of the present invention in both genders.

The comparable response of the VNO in men and women to the inventive weight enhancing composition is a strong predictor that pre-pubertal girls and menopausal women, and well as children, will benefit from the inventive composition. Significantly, several experimental trials indicated that the invention has no effect on LH, FSH or other hormones specific to pre-menopausal women (see Example 3 below). The lack of reproductive hormone modification by the present invention suggests its effect will not be limited to pre-menopausal women.

The invention elicits an unusually strong response in the VNO, as compared to other pharmacologically active vomeropherins. This robust response was the motivation for the initial studies to test for the possibility of gonadotrophic hormone release effects. For instance, there was a VNO response to a preferred embodiment of the present invention, $(17\beta)19$-norpregna-1,3,5(10)-trien-3-ol, of 30 mV in men and 50 mV in women (see Example 2 below). This result provides a reasonable predictor that the invention will be effective treatment for most target patient populations.

Dosage Levels. Effective dosage levels of the active ingredient of the invention when applied to the facial skin of the patient can be from about 1–100 $\mu$g, preferably about 10–50 $\mu$g, and most preferably about 20–30 $\mu$g. When the active ingredient is introduced directly into the VNO, an effective amount of the active ingredient is about 1 pg to about 1 ng, or preferably about 10 pg–50 pg. When the active ingredient is administered to the nasal passage by ointment, cream or aerosol, an effective amount is about 100 pg to about 100 $\mu$g, preferably about 1 ng to about 10 $\mu$g.

Treatment Protocols. For standard oral, IV or IM administered pharmaceuticals, it is well understood that there will be different dosage and treatment protocols for various classes of patients. For instance, in pediatric cases, the doses are often lower than in adult administration to accommodate body weight differences. Additionally, toxicity and clearance rates in children differ from those of adults. In geriatric and bed ridden patients, compromised drug clearance would also be taken into effect. This is also the case with renally deficient patients.

In the case of VNO active drugs, there are also differences in patient groups for dosages, timing, and other drug administration considerations. However, certain considerations are much less critical with VNO medications. For instance, body size is much less of a factor in determining dosages. Clearance rates are not compromised by renal dysfunction. Thus, the VNO as a drug administration site has advantages in regards to these considerations. In some cases it is still appropriate to provide adjustments to dosage levels for various patent groups. These modifications will be easily ascertained by one of ordinary skill in the art, such as by experimentation with dose and time of dose.

Means of Administration. As described previously in the prior art section of this application, administration of pharmaceuticals via the VNO has many unique advantages over standard drug administration. The doses administered are of extraordinary small sizes, allowing unique approaches to dosing techniques. Because there is de minimis systemic exposure to these medications, concerns about drug interactions, prenatal exposure for administration to pregnant women, juvenile sensitivity, and other common challenges are dramatically decreased or eliminated altogether.

Single Dose Administration. The weight promoting method of the present invention enjoys the unique advantages of VNO administration. There are a variety of embodiments for methods of administration of the invention, and products for practicing these methods, including suitable dispensers. A simple nasal spray bottle can provide a dose, similar to those used to administer nasal decongestants, typically calling for a water soluble derivative of the active compound. For a more measured dose, a propellant bottle similar to those used for asthma drug administration can be employed. The latter administration method typically uses a hydrophobic derivative of the inventive compound.

While there may be a cumulative effect of exposure to the active ingredient, spiked dose administration can be used to coordinate with schedules or natural rhythms to produce an enhanced effect. For instance, pregnant women with all-day "morning sickness" will often have specific periods during the day, typically in late evening, when their nausea is less acute. If the woman administers the active ingredient in anticipation of this time, her increased appetite can be timed to the most useful period.

Similarly, high-strung squeamish teenage eaters may have a period during the day in which they are calmer and less prone to eating disorders. This will often occur when they are removed from the stress of school, for instance, or if they have a habit of late evening snacking. Again, the dosage of the active ingredient could be timed to optimize this opportunity of predilection towards food intake. Infants suffering from eating disorders will also have periods of the day more amenable to successful feeding.

Single dose exposure to the active ingredient can be administered as a dry powder, in much the same way as snuff. A preferable means of administration is use of a metered device. Rather than use a pure form, this form of administration would typically have the active ingredient on a carrier. This approach is preferable because the effect of small dosages of the inventions active ingredient is so intense that the carrier may be needed to provide an appropriate dosage and avoid overdosing.

Where the dose levels are varied, breakable capsules can be employed. This means of administration proves measured single dose exposure. The breakable capsules can be provided on a bubble pack card, with the days or times of the doses stamped next to the appropriately measured dose. For instance, the optimal time lag prior to a scheduled meal can be printed next to the appropriate dose.

Continuous and Pulsatile Dose Administration—It is possible to administer the active ingredient into the sinuses. The ingredient naturally descends into the nose, providing a continuous dose of the ingredient to the VNO. This sinus loading approach has been employed experimentally in rats by the present inventors.

Other approaches of continuous or pulsatile dosing can include providing a gel or pad containing the active ingredient in the nose. These administration approaches provide retention of the active ingredient in the nose for an extended period of time, providing continuous exposure. The active ingredient can also be encapsulated in a slow release or timed release form, avoiding the potential problem of fatigue and attendant rebound effects.

The present invention can be administered in the form of an ointment. This approach to administration will also provide a long term effect. Therefore, the ointment embodiment of the present invention would typically be applied near, but not on, the VNO. Appropriate placement would be on the upper lip. The ointment allows a longer lasting exposure to the active ingredient than certain other approaches.

Administration with Other Treatment. Patients that would benefit from the invention are often being treated by other means. Respiratory exposure devices can provide simultaneous administration of the active ingredient with other substances. For instance, chronically ill patients are often provided with supplemental oxygen, either in an oxygen tent, or through nasal tubes. Such patients may be ambulatory, carrying their oxygen units with them. Respirators are often used in very ill, bed ridden patients.

Respiratory administration units may be supplement with a dose of the active ingredient for ease of administration by introduction into the air stream. This airborne administration can provide concurrent single, measured doses, or exposure on a continuous basis.

Because of the relatively stable chemical structure of the active ingredient, numerous means of administration are useful. Nebulizers, vaporizers, sonicators and other devices which produce an airborne mist can also be used to administer appropriate doses of the active ingredient, again either in measured doses, or on a continuous bases. A continuous institutional dose in specific rooms in nursing homes can be provided where humidifier or other air circulating mechanisms are currently employed.

Pulsatile Dose Exposure. One potential pitfall to continuous exposure of the VNO to the active ingredient is the potential for VNO receptor fatigue, and a potential rebound effect after cessation of administration. Several administration techniques can be used to avoid this potential problem A simple and elegant approach to providing a pulsatile exposure is to have the dose flow with normal breathing. For instance, the active ingredient in a suitable carrier (e.g. an alcohol-based solution or gel) can be swabbed on the upper lip. Then, with each nasal breath, there is an intermittent exposure to the material. Placing a gel or pad containing the active ingredient near, but not directly at, the VNO would also serve to provide intermittent exposure.

In some conditions, it may be preferable to have a more continuous exposure to the active ingredient, or a low level continues exposure with intermittent higher level exposure peaks. The appropriate treatment protocol will become apparent when using standard optimization criteria.

Active Ingredient

Compound Structure. In the present application, a "pregnane" or "pregnane steroid" refers to a polycyclic hydrocarbon with a four-ring steroidal structure with methylation at the 10- and 13-positions, and ethylation (including unsaturated groups) at the 17-position. The 19-norpregnanes lack a methyl or other carbon-containing substituent on C-10 where C-19 would normally be found. 19-norpregnenes are a subset of pregnanes and contain at least one double bond. The following structure shows the four-ring steroidal structure common to 19-norpregnanes (which, as already mentioned, include the pregnenes). In describing the location of groups and substituents, the following numbering system is employed:

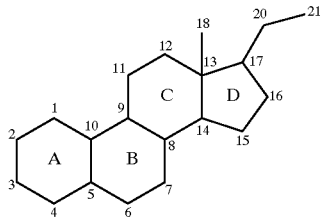

The active ingredient of the present invention has the general structure:

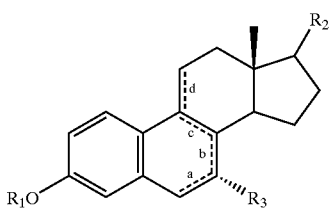

(I)

where
$R_1$=H, $C_{1-4}$ alkyl, $C_{1-4}$ alkanoyl, $SO_3H$, or salts thereof,
$R_2$=$C_{1-4}$alkyl,
$R_3$=H or methyl, and one or two non-adjacent members of a, b, c, and d are optional double bonds.

The 13- and 17-positions are chiral centers. In the present application, unless the contrary is indicated, reference to a compound of formula (I) will be used to mean that the 13-methyl is 13β, while the 17-ethyl can be either α or β (when one or the other only is being referenced, then it will be specifically identified as the 17α or 17β diastereomer). The compound 19-norpregna-1,3,5(10)-trien-3-ol has the structure illustrated in formula (I) above in which $R_1$ is H, $R_2$ is ethyl, and $R_3$ is H, and none of the optional double bonds are present. Thus the name 19-norpregna-1,3,5(10)-trien-3-ol, without more, requires either 17α or 17β substitution.

The particular compound (17β)19-norpregna-1,3,5(10)-trien-3-ol therefore has the structure (Ia) below:

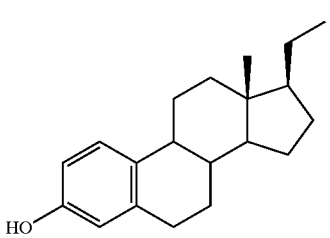

(Ia)

Syntheses of compounds of the type of formula (I), and particularly (Ia), are described in detail in Jennings-White et al;, U.S. Pat. No. 5,792,757. The disclosures of this and other documents referred to elsewhere in this application are incorporated herein by reference. The compound of formula (Ia) represents a preferred embodiment of the present invention. Other preferred embodiments include 17β-methylestra-1,3,5(10)-trien-3-ol, and 21-methyl-19-norpregna-1,3,5(10)-trien-3-ol.

It will be understood that some substituents may be allowed (such as halogen) on compounds of the present invention, provided they still promote weight or appetite gain in a person.

Synthesis of Active Ingredients. Compounds related to certain of the compounds employed in the weight promoting composition of the present invention have been disclosed in the prior art. These art teachings provide for clinical application distinctly divergent from that of the weight promoting composition of the present invention. Reflecting these prior art therapeutic approaches, these compounds are taught as being administered in a composition which would be ineffective or inappropriate for use in the inventive weight promoting method. Similarly, the compositions containing certain of the compounds used in the present inventive composition are dissimilar. The present composition must be specifically configured to provide appropriate VNO administration.

An appropriate scheme which can be modified to produce the preferred active components of the subject invention can be found in Crowe et al., U.S. Pat. No. 3,946,052. The final compound produced in this patent was 17-norpregna-1,3,5(10)-trien-3-ol, and lower alkyl homologues of this component are also mentioned. The 17β subsistent is described in these documents as being methyl, ethyl, propyl, or butyl. Further work provided other synthesis schemes, as shown in Peters et al., *J. Med. Chem.*, 32, 1642 (1989).

While Crowe et al. is useful in teaching a synthetic scheme related to this general class of compounds, the application for the compound taught by Crowe et al. is highly divergent from that of the inventive weight promoting composition. Crowe et al. teaches that their compounds should be used as an orally administered contraceptive. Crowe et al. also teaches a dosage level many orders of magnitude above those appropriate for the present invention, that is a in daily doses of between 0.01 mg to 5 mg.

The synthesis procedure developed by the inventors to produce the potassium salt of the sulfate compound to the inventive composition is set forth in Example 1, below. This derivative was designed to provide increased water solubility.

The synthetic procedures for pregnanes of formula I where $R_1$ is $C_{1-4}$ alkyl or alkanoyl will be well known to those skilled in the art. The pregnanes where $R_1$ is $C_{1-4}$ alkyl, especially methyl, are expected to possess enhanced volatility, which is significant for certain delivery modes, such as the actively propelled inhalers described above.

EXAMPLE 1

Synthesis of 19-Norpregna-1,3,5(10)-trien-3-yl Sulfate Potassium Salt

The following synthetic method provides for the potassium salt form of one embodiment of the active ingredient. This compound enjoys an increased water solubility, and so is well suited for a water based carrier.

Sulfur trioxide/pyridine complex (1.91 g, 12.0 mmol) was added to 19-norpregna-1,3,5(10)-trien-3-ol (568.9 mg, 2.0 mmol) in 5 mL of dry dimethylformamide (stored over molecular sieves). After stirring 4 hours, the suspension was added dropwise, with rapid stirring to triethanolamine (5.97 g, 40.0 mmol) in 100 mL of water, and the resulting solution was filtered through Celite® 503 filter aid. The filtrate was added to potassium carbonate (3.56 g, 25.8 mmol) in 10 mL of water with rapid stirring and then filtered through a coarse glass frit. The residue was washed with 10 mL of water and 10 mL of acetone and then dried over $P_2O_5$ under vacuum to give a tan solid (1.0179 g, 2.528 mmol, 126%), m.p. 221→250° C.

EXAMPLE 2

Screening Trials for VNO Reactivity to (17β)19-Norpregna-1,3,5(10)-trien-3-ol

In Vitro Study CL002. This study was conducted using VNO cells that had been collected from healthy male and female volunteers. It was found that cells from both men and women responded to application of (17β)19-norpregna-1,3,5(10)-trien-3-ol with development of an inward current, and that the magnitude of this current was dose dependent. At (17β)19-norpregna-1,3,5(10)-trien-3-ol concentrations of $10^{-7}$ M and higher this response was significantly different from the control response. In addition, the magnitude of the response was greater in cells from women than in cells from men.

The peak effect was observed at a concentration of $10^{-5}$ M, at which point the mean peak inward current was 96 pA in cells from women and 55 pA in cells from men.

In Vivo Study CL001. This study was conducted in healthy male and female volunteers each tested with a single dose of (17β)19-norpregna-1,3,5(10)-trien-3-ol. The mean peak amplitude of the EVG (electrovomerogram) response to intranasal administration of (17β)19-norpregna-1,3,5(10)-trien-3-ol, reported as the magnitude of the difference from the response to placebo, was 30 mV in men and 50 mV in women (13.9 mV in women and 5.3 mV in men difference from the response to placebo). In both genders the peak amplitude of the response to (17β)19-norpregna-1,3,5(10)-trien-3-ol was significantly greater than that to placebo. In addition, the peak amplitude of the response in women was greater than that in men.

Methods: For VNO stimulation, a $10^{-8}$ M solution of (17β)19-norpregna-1,3,5(10)-trien-3-ol vomeropherin was prepared in propylene glycol (PG). A vapor pulse (duration: 2 seconds) of the vomeropherin was obtained bubbling clean air through the solution (air flow: 3 mL/min.). This delivered an estimated quantity of 200 pg of (17β)19-norpregna-1,3,5(10)-trien-3-ol to the VNO. The control was a pulse of PG alone in vapor form.

Processing and analysis of the results was done off-line. The amplitude or frequency of the different parameters was measured. The mean and standard deviation of the mean were obtain for all parameters 5 minutes after stimulation with control, and (17β)19-norpregna-1,3,5(10)-trien-3-ol. The significance of the results was studied using the paired, two-tailed student t-test, and analysis of variance.

Data Analysis: The following is a summary of the results in female subjects: EVG: 13.8 mV, electrodermal activity (EDA): +109.4 μS, Respiratory frequency (RF) +3.0 cycles/min, cardiac frequency (CF): 0 beats/min, electromyogram (EMG) 0 Hz, body temperature (BT): +0.2° C., alpha-cortical activity (α-CA): +35.8 μV$^2$/Hz, beta-cortical activity (β-CA): −2.2 μV$^2$/Hz. In summary, the performance is EVG++, EDA+, α-CA++, where + indicates a moderate increase in activity and ++ indicates a substantial increase in activity. These numbers show the mean effect of (17β)19-norpregna-1,3,5(10)-trien-3-ol subtracted from the mean effect of placebo, for each biological parameter measured.

In eight female subjects vomeropherin (17β)19-norpregna-1,3,5(10)-trien-3-ol (200 pg) induced a robust mean EVG followed by changes in some autonomic parameters and EEG. EDA increased significantly from placebo, and from the mean male EVG (p<0.05). This was followed by changes in some autonomic parameters and EEG. EDA increased significantly from placebo (p<0.05). Alpha rhythm recorded from T4A2 increased significantly from placebo (p<0.05). This coexisted with decreased beta rhythm in CA2 (p<0.05), as compared to the effect of placebo. Other autonomic parameters and EMG remained unchanged.

The following is a summary of results in six male subjects; EVG: +5.3, EDA: +79.1, RF: −1.7, CF: 0, EMG: 0, BT: −1.2, α-CA: −11.7, β-CA: −−64.9. The performance for (17β)19-norpregna-1,3,5(10)-trien-3-ol in this study may be summarized as EVG+, EDA+, β-CA−−. These numbers show the mean effect of (1.7p)19-norpregna-1,3,5(10)-trien-3-ol subtracted from the mean effect of placebo, for each biological parameter measured.

In men, (17β)19-norpregna-1,3,5(10)-trien-3-ol produced a mean EVG response significantly different from placebo (p<0.05), but also smaller than that recorded in female volunteers. This was followed by increased EDA (p<0.05), but in a lesser amount than the EDA change observed in female subjects. Body temperature and alpha rhythm also decreased in male subjects treated with (17β)19-norpregna-1,3,5(10)-trien-3-ol (p<0.05) as compared to placebo. Other biological parameters did not change significantly in males.

Conclusions: Vomeropherin (17β)19-norpregna-1,3,5(10)-trien-3-ol is active in the VNO of both female and male subjects. The autonomic, EEG changes induced are smaller, compared to the effects of other vomeropherins with known psychotropic effects. In female subjects, (17β)19-norpregna-1,3,5(10)-trien-3-ol induced a large EVG followed by increased EDA and alpha brain waves, and decreased beta waves.

Both study CL001 and study CL002 are consistent in indicating that VNOs from both genders respond to (17β)19-norpregna-1,3,5(10)-trien-3-ol. The magnitude of this response is greater in females than in males.

EXAMPLE 3

Gonadotropin Secretion Study (Discovery of Weight Promotion Activity)

Study CL003 was designed to investigate possible effects of (17β)19-norpregna-1,3,5(10)-trien-3-ol on gonadotropin secretion in healthy female volunteers. Because gonadotropins typically are secreted in a pulsatile pattern with 4–6 peaks per day, (17β)19-norpregna-1,3,5(10)-trien-3-ol was administered at 10-minute intervals over a 6-hour period. This timing was provided in order to determine whether (17β)19-norpregna-1,3,5(10)-trien-3-ol affected the pattern of pulsatility and/or the magnitude of the gonadotropin release. No consistent changes in gonadotropin secretion were observed, and no changes in menstrual cycle pattern or ovulation were observed.

Unexpectedly, the investigators received spontaneous, anecdotal post-study reports from the subjects indicating that they had experienced increased appetite. To follow up on these anecdotal reports, the investigators gave the subjects a questionnaire one month after completing their participation in the study to assess this effect of (17β)19-norpregna-1,3,5(10)-trien-3-ol in a systematic fashion. All subjects indicated they had experienced a large increase in appetite, which was associated with the (17β)19-norpregna-1,3,5(10)-trien-3-ol treatment arm of the study.

EXAMPLE 4

Follow-on Weight Promotion Studies

Study CL004. Study CL004 was conducted as a follow-on to the surprising appetite results of study CL003, and was designed to provide a more focused investigation of the effects of (17β)19-norpregna-1,3,5(10)-trien-3-ol on appetite. In the interest of providing a comparable investigatory scheme as the initial study, the same dosing regimen (one dose every 10 minutes for 6 hours) was used as had been used for study CL003.

Study CL004 was conducted after study CL003 had been completed. The interim findings are that all subjects in this study reported an increase in appetite for at least one week after administration of (17β)19-norpregna-1,3,5(10)-trien-3-ol but not after administration of placebo. This increase in appetite was associated with a persistent increase in body weight.

Study CL005. Study CL005 was designed to investigate in detail the effects of (17β)19-norpregna-1,3,5(10)-trien-3-ol -on food consumption in studies CL003 and CL004. The (17β)19-norpregna-1,3,5(10)-trien-3-ol dosing regimen was the same as had been used for the previous studies. Food intake and appetite were examined in this study in great detail. Subjects kept records of their appetite, food intake, etc., over a 3–4 month period. The preliminary data analysis indicates that administration of (17β)19-norpregna-1,3,5 (10)-trien-3-ol, but not administration of placebo, was associated with a perceived increase in appetite for at least one week after drug administration.

Study CL006. Study CL006 was designed to provide an evaluation of a more clinically meaningful (17β)19-norpregna-1,3,5(10)-trien-3-ol dosing regimen, as well as to provide a more controlled environment in which to evaluate appetite and food intake effects. In this study, subjects received (17β)19-norpregna-1,3,5(10)-trien-3-ol in association with mealtimes, and they remained in a metabolic unit throughout the study. An informal analysis during this study in progress of the blinded data suggests that some participants experienced a treatment-related increase in food intake and body weight.

While this invention has been described in connection with certain preferred embodiments, it will be evident to one of ordinary skill in the art that certain equivalent compositions, methods, and products may be substituted with similar efficacy, and such equivalents are intended to be encompassed within the following claims.

We claim:

1. A method of promoting weight, comprising administering to the vomeronasal organ of a human a pregnane in an amount effective to promote weight by contact with the vomeronasal organ but ineffective to promote weight by systemic absorption into the circulatory system, where the pregnane has the formula:

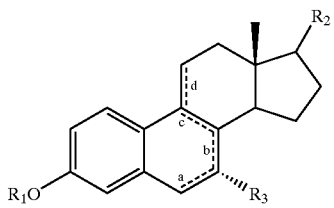

where
$R_1$=H, $C_{1-4}$ alkyl, $C_{1-4}$ alkanoyl, $SO_3H$, or a salt thereof,
$R_2$=$C_{1-4}$ alkyl,
$R_3$=H or methyl, and
one or two non-adjacent members of a, b, c, and d are optional double bonds.

2. The method of claim 1, where the human suffers from a disease associated with weight loss.

3. The method of claim 2, where the disease associated with weight loss is anorexia nervosa, anosmia, wasting in elderly, AIDS, cancer, morning sickness, osteoporosis, renal disease, or a childhood eating disorder.

4. The method of claim 1, where the human is an athlete.

5. The method of claim 4, where the athlete participates in wrestling, body building, football, hockey, or weight lifting.

6. The method of claim 1, where the amount of the pregnane administered is from 1 pg to 100 μg per unit dose.

7. The method of claim 1, where the pregnane is administered to the vomeronasal organ by being applied to the facial skin of the human near the vomeronasal organ.

8. The method of claim 7, where the amount of the pregnane administered is from 1 μg to 100 μg per unit dose.

9. The method of claim 8, where the amount of the pregnane administered is from 10 μg to 50 μg per unit dose.

10. The method of claim 9, where the amount of the pregnane administered is from 20 μg to 30 μg per unit dose.

11. The method of claim 1, where the pregnane is administered to the vomeronasal organ by being introduced directly to the vomeronasal organ of the human.

12. The method of claim 11, where the amount of the pregnane administered is from 1 pg to 1 ng per unit dose.

13. The method of claim 12, where the amount of the pregnane administered is from 10 pg to 50 pg per unit dose.

14. The method of claim 1, where the pregnane is administered to the vomeronasal organ by being introduced to the nasal passage of the human in an ointment, cream, or aerosol.

15. The method of claim 14, where the amount of the pregnane administered is from 100 pg to 100 μg per unit dose.

16. The method of claim 15, where the amount of the pregnane administered is from about 1 ng to about 10 μg per unit dose.

17. The method of claim 1 where the pregnane is (17β) 19-norpregna-1,3,5(10)-trien-3-ol.

18. The method of claim 1 where the pregnane is (1/β)-methylestra-1,3,5(10)-trien-3-ol.

19. The method of claim 1 where the pregnane is 21-methyl-19-norpregna-1,3,5(10)-trien-3-ol.

20. The method of claim 2 where the pregnane is (17β) 19-norpregna-1,3,5(10)-trien-3-ol.

21. The method of claim 2 where the pregnane is (17β)-methylestra-1,3,5(10)-trien-3-ol.

22. The method of claim 2 where the pregnane is 21-methyl-19-norpregna-1,3,5(10)-trien-3-ol.

* * * * *